United States Patent [19]

Ecke

[11] 4,064,178
[45] Dec. 20, 1977

[54] BIS(4-CHLOROPHENYL)METHYL METHYL SULFOXIDE

[75] Inventor: George G. Ecke, Barberton, Ohio

[73] Assignee: PPG Industries, Inc., Pittsburgh, Pa.

[21] Appl. No.: 701,383

[22] Filed: June 30, 1976

Related U.S. Application Data

[63] Continuation-in-part of Ser. No. 578,598, May 19, 1975, abandoned.

[51] Int. Cl.$^2$ .................... C07C 147/14; A01N 9/14
[52] U.S. Cl. ........................ 260/607 AR; 424/337
[58] Field of Search ............ 260/607 A, 607 AR; 424/337

[56] References Cited

U.S. PATENT DOCUMENTS

| | | | |
|---|---|---|---|
| 2,618,640 | 11/1952 | Archer et al. | 260/293.4 |
| 3,016,403 | 1/1962 | Dodson | 260/607 |
| 3,054,719 | 9/1972 | Hendrik et al. | 427/337 |
| 3,412,149 | 11/1968 | Schlör et al. | 260/556 |
| 3,415,887 | 12/1968 | Keogh et al. | 260/607 |
| 3,465,044 | 9/1969 | Hirano et al. | 260/607 |
| 3,466,377 | 9/1969 | Shunk et al. | 424/337 |
| 3,549,702 | 12/1970 | Loev | 260/556 |
| 3,615,745 | 10/1971 | Crovetti et al. | 260/607 X |
| 3,624,094 | 11/1971 | Gautier et al. | 260/607 A X |
| 3,637,803 | 1/1972 | Shen et al. | 260/470 |
| 3,689,567 | 9/1972 | Shen et al. | 260/607 A |

FOREIGN PATENT DOCUMENTS 1,178,279   1/1970   United Kingdom.

OTHER PUBLICATIONS

C.A., 72, 1970, Shen et al., 3223x.
C.A., 56, (1962), Corey et al., 15335b.
Klenk et al., JACS, 70 (1948), pp. 3846-3850.
Metcalf et al., Bulletin World Health Organization, vol. 38, pp. 633-647 (1968).

Primary Examiner—Joseph Paul Brust
Assistant Examiner—Molly C. Eakin
Attorney, Agent, or Firm—Robert J. Grassi

[57] ABSTRACT

Bis(4-chlorophenyl)methyl methyl sulfoxide which effectively controls the harmful effects upon plants of plant pests, particularly Mexican Bean Beetle and Southern Army Worm, as well as certain fungi and bacteria is disclosed; as well as, the method of controlling the harmful effects of plant pests with the compound.

1 Claim, No Drawings

BIS(4-CHLOROPHENYL)METHYL METHYL SULFOXIDE

CROSS REFERENCE TO RELATED APPLICATIONS

This application is a continuation-in-part of copending application Ser. No. 578,598, filed May 19, 1975 now abandoned.

BACKGROUND OF THE INVENTION

1. Field of the Invention

The invention relates to phenyl sulfoxides, in particular bis(4-chlorophenyl)methyl methyl sulfoxide, and to the method of controlling the harmful effects of plant pests on plants with the compound, particularly, Mexican Bean Beetle, Southern Army Worm, as well as certain fungi and bacteria.

2. Description of the Prior Art

Plant pests harmfully affect crops and ornamentals, so that agricultural techniques such as applying chemicals to the plant are required to control these harmful effects. However, most affects of chemicals upon living systems are not a priori predictable. Although sulfides, sulfoxides, and sulfones are known in the prior art, there appears to be nothing in the prior art which suggests or teaches that the harmful effects of insects such as Mexican Bean Beetle or the Southern Army Worm as well as certain bacteria and fungi would be controlled by the particular compound bis(4-chlorophenyl)methyl methyl sulfoxide.

The following patents and references describe known sulfides, sulfoxides, and sulfones, as well as certain of their properties. Bis(4-chlorophenyl)methyl methyl sulfide is described as being active against the mosquito species, *Anopheles albimanus*, by R. L. Metcalf et al, *Bulletin of the World Health Organization*, Vol. 38, pages 633–647, (1968). Phenylmercaptomethane sulfonamide is described as being active against *Phytophthora infestans* (U.S. Pat. No. 3,412,149). Oximidomethane sulfonamides are disclosed as being active against bacteria and weeds (U.S. Pat. No. 3,549,702). 4-Methoxyphenyl diiodomethyl sulfone is shown to inhibit the growth of *Aspergillus oryzae* (U.S. Pat. No. 3,615,745), and 2,4,5,4'-tetrachlorodiphenyl sulfide, sulfoxide, and sulfones are shown to be effective against Red Spider Mites (U.S. Pat. No. 3,054,719). Other sulfones, sulfides, and sulfoxides are described but their activity against fungus are not known. For example, compounds of type B—X—C-(Ar)(Ar')-SO$_2$-R wherein B is a lower aliphatic tertiary-amino group, X is a lower alkylene group, Ar and Ar' are aryl groups and R is an alkyl group, are claimed as analgetics. 4,4'-Chlorodiphenyl sulfone is claimed as an important monomer for preparing polyarylene polyethers (Belgian Pat. No. 650,476). Certain aryl sulfoxides are described by C. Shunk et at (U.S. Pat. No. 3,466,377) as being analgetics. Other aryl sulfones are described as both analgetics and anti-pyretics by C. Shunk et al (U.S. Pat. Nos. 3,637,803 and 3,689,567), Jean A. Gautier et al in U.S. Pat. No. 3,624,094 describes alpha-[(phenyl sulfinyl) methyl]-alpha phenyl derivatives of pyridinemethanols as analgetics and anti-inflammatory agents.

SUMMARY OF THE INVENTION

The novel sulfoxide bis(4-chlorophenyl)methyl methyl sulfoxide effectively controls the harmful effects of certain plant pests upon plants. These plant pests are insects such as Mexican Bean Beetle, Southern Army Worm, and fungi such as *Fusarium, Phytophthora infestans,* and bacteria such as *Xanthomonas vesicatoria.* These are controlled by contacting the plants with bis(4-chlorophenyl)methyl methyl sulfoxide in an amount effective to control the harmful effects of the plant pests upon plants.

DESCRIPTION OF THE PREFERRED EMBODIMENTS

Bis(4-chlorophenyl)methyl methyl sulfoxide (bis(p-chlorophenyl) methyl methyl sulfoxide), which is represented by the structural formula:

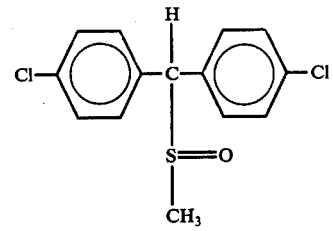

is synthesized from 4,4'-dichlorobenzophenone as illustrated in Example I.

EXAMPLE I

SYNTHESIS OF BIS(P-CHLOROPHENYL)METHYL METHYL SULFOXIDE

Hydrogenation of 4,4'-Dichlorobenzophenone to 4,4'-Dichlorobenzhydrol

Sodium borohydride (0.164 mole) 6.25 grams in 300 ml. of ethanol was slowly added (over a 30 minute period) to a refluxing solution of 74.3 grams (0.296 mole) of 4,4'-dichlorobenzophenone (Eastman 1440) in 250 ml. of ethanol, and refluxing was continued for an additional 30 minutes. Then a 100 ml. aqueous solution containing 43.5 grams of acetic acid was added dropwise until hydrogen evolution stopped, whereupon the remainder was rapidly added. A white precipitate formed and was collected by filtration. A 300 ml. aqueous slurry containing this precipitate was warmed to above 95° C., cooled, and filtered, and 74.1 grams (99 percent) of a white solid product (4,4'-dichlorobenzhydrol) having a melting point of 92.5°–94° C. was obtained.

Preparation of Chloro-bis(p-chlorophenyl)methane

A solution of 60.02 grams (0.237 mole) of the 4,4'-dichlorobenzhydrol (prepared above) in 175 ml. of toluene, was refluxed and distilled to remove traces of water; then 42 grams (0.356 mole) of thionyl chloride under anhydrous conditions was slowly added during a one hour period. The solution was refluxed and then distilled to remove excess thionyl chloride. The remaining solvent was removed by distillation under vacuum.

The crude product (68.9 grams) was recrystallized twice from 2,2,4-trimethylpentane to give 49.2 grams (76 percent) of chloro-bis(p-chlorophenyl)methane, melting point 61.5°–62.5° C.

Preparation of Bis(p-chlorophenyl)methyl methyl sulfide

Chloro-bis(p-chlorophenyl)methane (prepared above) (0.130 mole, 35.2 grams) was added to a cold sodium mercaptide solution formed by distilling 0.205 mole (9.8 grams) of methyl mercaptan into a stirred, cooled solution (0° C.) of ethanolic sodium ethoxide (157 ml., 1.038 N, 0.163 grams). Upon warming, a precipitate of sodium chloride formed, and after refluxing this mixture for 2 hours and then mixing with water, an oil formed which was extracted with three portions of methylene chloride (30 ml.). The methylene chloride solvent was distilled off under vacuum, leaving 36.7 grams (100 percent) of a white solid with a melting point of 55.5°–57° C. Recrystallization from 2,2,4-trimethylpentane at 0° C. gave a 92 percent yield of the white solid bis(p-chlorophenyl)methyl methyl sulfide (melting point 56°–57° C.).

Analysis Calculated For: $C_{14}H_{12}Cl_2S$: C, 59.37; H, 4.27; and S, 11.32. Found: C, 59.25; H, 4.20; and S, 11.1.

Preparation of Bis(p-chlorophenyl)methyl methyl sulfoxide

A solution of 10.7 grams (0.0525 mole) of m-chloroperbenzoic acid in 150 ml. of chloroform was slowly added to a cool solution (5°–7° C.) of 14.1 grams (0.050 mole) of bis(p-chlorophenyl)methyl methyl sulfide (prepared above) in 500 ml. of chloroform, and the resulting solution stirred for 2 hours at a temperature of 5° C., while a white precipitate formed. The mixture after warming to ambient temperature and holding at this temperature for a 2 hour period was then mixed with a solution having 20 grams of potassium carbonate in 200 ml. of water. The chloroform phase was then removed and washed with 100 ml. of water, and the chloroform distilled off; the vacuum distillation leaving 14.7 grams of a crude product which was recrystallized twice from 2,2,4-trimethylpentane-benzene (2:1) mixture to yield 11.7 grams (78 percent) of the white colored solid bis(p-chlorophenyl)methyl methyl sulfoxide with a melting point of 109.5°–110.5° C.

Analysis Calculated For: $C_{14}H_{12}Cl_2OS$: C, 56.19; H, 4.04; and S, 10.72. Found: C, 56.18; H, 4.04; and S, 10.5.

a. Biological Properties

Bis(4-chlorophenyl)methyl methyl sulfoxide has exhibited useful biological activity against the harmful effects of plant pests on plants. An obnoxious plant pest whose harmful effects on plants is controlled by the compound is the Southern Army Worm (*Spodoptera eridania*), the following test procedure illustrates how its harmful effects on plants are controlled.

PROCEDURE

Potted horticultural bean plants (*Phaseolus vulgaris* L.) at a growth stage where the primary leaves are 2.5 inches long, were dipped into a slightly agitated solution or suspension of the test compound, air-dried, placed in a greenhouse, and watered by a subterranean source. After drying, the plants were infested with 7 day old fourth (4th) instar larvae of the Southern Army Worm (*Spodoptera eridania*), which are about ⅜ inch long, by enclosing the plant within a spherical wire mesh cage containing the larvae. Five larvae are used per replicate of the test, and at least three replicates are used.

After 72 hours the larvae are observed for mortality or other significant physiological effects, such as distorted growth.

The effectiveness of the compound at the test concentration is expressed as percent control calculated as follows:

Percent Control = $\frac{\text{(number of dead larvae on all plants)}}{\text{(total number of larvae on all plants)}} \times 100$ percent Table I shows the test results obtained. Column 1 gives the example number, column 2 gives the name of the compound which was synthesized as described herein unless indicated otherwise, column 3 gives the amount of test compound in the solution as parts per million (ppm), and column 4 gives the percent control of the Southern Army Worm.

In these tests 100 percent means complete control, all larvae killed and 0 percent means no control.

TABLE I

| PERCENT CONTROL OF SOUTHERN ARMY WORM | | | |
|---|---|---|---|
| | Test Compound | | |
| Example No. | Name | Concentration | Percent Control of Southern Army Worm |
| II | bis(phenyl)methyl methyl sulfoxide[a] | 1000 ppm | 0 |
| III | bis(4-chlorophenyl)methyl methyl sulfoxide | 1000 ppm | 100.00 |
| | | 500 ppm | 100.00 |

[a]known compound described in U.S. 2,618,640 b. Application to Control the Harmful Effects of Plant Pests on Plants With bis(4-chlorophenyl)methyl methyl sulfoxide 1. Other Plant Pests Whose Harmful Effects On Plants Are Controlled Bis(4-chlorophenyl)methyl methyl sulfoxide was discovered to be useful in controlling the harmful effects of other plant pests, such as insects of the genus *Epilichona* and *Spodoptera*, fungi of the genera *Phytophthora* and *Fusarium*, and bacteria of the genus *Xanthomonas*, and in particular the plant pest species *Epilichona varivestis* (Mexican Bean Beetle), *Phytophthora infestans* (Late Blight of Tomatoes), *Fusarium oxysporum f. lycopersici* (Fusarium Wilt of Tomatoes), and *Xanthomonas vesicatoria* (Bacterial Leaf Spot of Tomatoes).

2. Method of Control

The harmful effects of a plant pest upon a plant are controlled by contacting the plant with bis(4-chlorophenyl)methyl methyl sulfoxide in an amount effective to control the harmful effects of the plant pest upon the plant. The term "plant pest", as used herein and in the claims means insects, fungus, bacteria of the genera mentioned herein.

The phrase "contacting the plant with bis(4-chlorophenyl)methyl methyl sulfoxide" as used herein and in the claims refers to any method of causing the compound to contact the plant. This contact may be achieved by any of the known methods of applying compositions to plants, e.g., by spraying a solution or an emulsion upon the plants, dusting with granules of inert materials coated with bis(4-chlorophenyl)methyl methyl sulfoxide, or with granules of the compound itself. This contact may be made once or several times over the growing period of the plants to insure protection or eradication of the harmful effects of the plant pests. For control of Fusarium the compound can be applied to the soil near the roots of the plant so as to be taken up by the plant.

The phrase "in an amount effective to control the harmful effects of the plant pest upon the plant" as used herein and in the claims means that amount of the bis(4-chlorophenyl)methyl methyl sulfoxide, as the active ingredient of a formulation which contacts the plant, which controls, that is reduces the harmful effects of the plant pests. This amount will vary with the number and size of the plants, the temperature and humidity, or the season — whether rainy or dry, and severity of the infestation in the growing region.

The amount required for controlling the harmful effects of insects of the genera *Epilichona* and *Spodoptera* ranges from 200 parts per million to the amount tolerated by plants, which is about 50,000 parts per million when applied as a dust, or 25,000 parts per million when applied as spray. Normally this range is from 250 to 10,000 ppm, and generally it is from 500 to 5000 ppm as a spray or dust which coats the foliage. These same ranges are also required for the specific insects *Epilichona varivestis* (Mexican Bean Beetle) and *Spodoptera eridania* (Southern Army Worm).

For controlling the harmful effects of a fungus of the genera Phytophthora and Fusarium upon plants, the amount of bis(4-chlorophenyl)methyl methyl sulfoxide ranges from 100 parts per million (ppm) to 25,000 ppm whether applied as a dust or spray. Normally the range is from 500 to 15,000 parts per million, and generally this range is from 1000 to 5000 parts per million, as a spray or dust when applied to coat the foliage of the plant. These same ranges are used to control the fungi species of *Phytophthora infestans* (Late Blight of Tomatoes) and *Fusarium oxysporum f. lycopersici* (Fusarium Wilt of Tomatoes).

For controlling the harmful effects of a bacterium of the genus Xanthomonas, and the bacterium species *Xanthomonas vesicatoria* (Bacterial Leaf Spot of Tomatoes), the same amount mentioned above for control of the fungus of the genera *Phytophthora* and *Fusarium* is used.

The phrase "to control the harmful effects of a plant pest upon the plants" as used herein and in the claims means that the harmful effects are reduced so that a smaller percentage of plants contacted with bis(4-chlorophenyl)methyl methyl sulfoxide are affected by the plant pest as compared to plants not chemically treated. The percentage of plants not affected will be from 25 to 100 percent of the total plants. For fungi and bacteria this means that 25 to 100 percent of the plants are free from the disease caused by the fungi or bacteria. For insects this means that the plants have from 25 percent to 100 percent less insects than untreated plants.

3. Suitable Agricultural Formulations

Although bis(4-chlorophenyl)methyl methyl sulfoxide can be applied alone as a spray or as granules, it is preferred that it be formulated in combination with other ingredients to make a suitable agricultural composition for contacting the plant or the plant and plant pest, particularly the foliage of the plant.

In these formulations bis(4-chlorophenyl)methyl methyl sulfoxide will comprise from 0.1 to 99 weight percent of the formulations.

A suitable agricultural formulation is a solution composed of one or more solvents in which bis(4-chlorophenyl)methyl methyl sulfoxide are completely soluble, and which contains a surfactant such as TWEEN 20 ®, to increase the wettability of the solution. Other solutions would be aerial spray formulations such as pressurized spray solutions, e.g., aerosols, which use one or more low boiling dispersants solvents such as Freon. The amount of the compound in the solution will depend upon its or their solubility which is effected by the temperature and other ingredients.

Dusts, which also are suitable agricultural compositions, are mixtures of an active compound, e.g., bis(p-chlorophenyl)methyl methyl sulfoxide, with one or more finely powdered solids having an average particle size of less than 50 microns, such as talc, attapulgite clay, keiselguhr, and other organic and inorganic solids which act as dispersants and carriers for the compound. A typical dust formulation will contain from 1.0 to 10.0 parts by weight of bis(p-chlorophenyl)methyl methyl sulfoxide, and the balance of the composition is divided between the other ingredients. These dust formulations may be formulated for aerial spraying, by using relatively coarse powders or particles coated with the compounds.

Other suitable agricultural compositions are wettable powders which are finely divided particles dispersed in water or other liquids. The wettable powder is applied to the plant as a dry dust, or as a water or other liquid emulsion. Carriers suitable for wettable powder formulations are Fuller's Earth, kaolin clays, silicas, and other highly absorbent, readily wettable inorganic diluents. Wettable powders generally contain about 5 to 80 weight percent of the active ingredient, depending upon the carrier absorbency, and usually contain a small amount of a wetting, dispersing, or emulsifying agent to aid dispersion.

Representative surfactants for use as wetting, dispersing, and emulsifying agents in agricultural compositions are alkyl and alkylaryl sulfonates and sulfates and their alkali salts; polyethylene oxides, sulfoxided oils, fatty acid esters of polyhydric alcohols, and other surface active agents, e.g., TWEEN 20 ®, a commercial surfactant. These surfactants, when used, vary from 0.25 to 15 weight percent of the composition.

A useful wettable powder formulation, for example, comprises about 80.8 parts of bis(p-chlorophenyl)methyl methyl sulfoxide, 17.9 parts of attapulgite clay, and as wetting agents, 1.0 part of sodium lignosulfate and 0.3 parts of sulfonated aliphatic polyester. Another useful formulation contains 50 weight percent of the sulfoxide, about 40 weight percent of hydrated silica, and about 10 weight percent of emulsifiers chosen from those described above. The powder is produced by mixing the desired ingredients and milling them to a suitably fine particle size, such as 1 to 200 microns, but preferably under 74 microns.

All of the wettable powder formulations described may contain one or more compatible agriculturally suitable compounds such as herbicides, fertilizers, pesticides, bactericides, fungicides, or other ingredients which serve to enhance healthy growth of crops.

All of the wettable powder formulations described may be utilized, for example, by mixing the wettable powder formulation with a suitable quantity of water such as 4 to 20 gallons of water per pound of formulation (480 to 8,000 kilogram per cubic meter), and then applied to the crop by the use of aerial or land-based spraying equipment at practical rate, e.g., 10 to 100 gallons per acre (0.09 to 0.94 cubic meters per hectare). The spraying rate is coordinated with the amount of material to be applied in order to give the desired weight of active ingredient per unit of area.

Other suitable agricultural compositions are emulsifiable concentrates, which are liquid or paste compositions that are dispersible in water or other liquids. These types of compositions may consist of the sulfoxide and a surfactant, or a liquid or solid emulsifying agent, mentioned herein, as well as a liquid carrier, such as xylene, heavy aromatic naphthas or other nonvolatile organic solvents. These emulsifiable concentrates are generally dispersed in a liquid carrier, e.g., water, and applied as a spray to the foliage of the plant to be treated. The weight percent of bis(p-chlorophenyl)methyl methyl sulfoxide in these concentrations varies with the application procedure, but is generally from 0.5 to 95 weight percent.

It is preferable to apply the sulfoxide to the plant prior to infestation by the plant pests, particularly the fungus or bacterium, and preferably before the larvae of the insects become adults.

While the invention has been described with reference to specific details for certain illustrative embodiments it is not intended that it shall be limited thereby except insofar as such details appear in the accompanying claims.

I claim:
1. Bis(4-chlorophenyl)methyl methyl sulfoxide.